United States Patent [19]

Niemers et al.

[11] Patent Number: 4,636,497

[45] Date of Patent: Jan. 13, 1987

[54] ANTI-THROMBOTIC PHARMACEUTICAL COMPOSITIONS COMPRISING TRICYCLO-4H-1,4-BENZOTHIAZINE DERIVATIVES AND METHOD OF USE THEREFOR

[75] Inventors: Ekkehard Niemers, Wuppertal; Rudi Grützmann, Solingen; Mithat Mardin, Wuppertal, all of Fed. Rep. of Germany; Wolf-Dieter Busse, West Haven, Conn.; Horst Meyer, Wuppertal, Fed. Rep. of Germany

[73] Assignee: Bayer Aktiengesellschaft, Leverkusen, Fed. Rep. of Germany

[21] Appl. No.: 770,895

[22] Filed: Aug. 29, 1985

Related U.S. Application Data

[63] Continuation of Ser. No. 517,081, Jul. 22, 1983, abandoned.

[30] Foreign Application Priority Data

Aug. 4, 1982 [DE] Fed. Rep. of Germany ....... 3229122

[51] Int. Cl.$^4$ .................. A61K 31/38; C07D 279/10; C07D 513/04

[52] U.S. Cl. ................... 514/215; 514/222; 514/223; 514/224; 540/521; 540/578; 544/32; 544/37; 544/38; 544/39

[58] Field of Search ....... 544/32, 37, 38, 39; 514/215, 222, 223, 224; 260/239 BE

[56] References Cited

U.S. PATENT DOCUMENTS 3,422,101  1/1969  Carson .................... 544/32
4,512,990  4/1985  Nelson et al. ............ 544/52

OTHER PUBLICATIONS

Jain et al, C.A. 100:120987, vol. 100, 1984, p. 586.
Gilchrist et al, C.A., vol. 97, 97:23716e, p. 706.
Miyano et al, CA, vol. 85, 1982, 85:94294d, p. 629.
Shuedov et al, C.A., vol. 78, 1973, 78: 43395k, p. 485.

*Primary Examiner*—Henry R. Jiles
*Assistant Examiner*—J. G. Mullins
*Attorney, Agent, or Firm*—Sprung Horn Kramer & Woods

[57] ABSTRACT

The present invention refers to novel anellated 4H-1,4-benzothiazines, several processes for the synthesis thereof, their use as pharmaceutical agents, in particular their use as lipoxygenase-inhibiting agents, pharmaceutical compositions containing the novel benzothiazines and a process for their manufacture.

2 Claims, No Drawings

ANTI-THROMBOTIC PHARMACEUTICAL COMPOSITIONS COMPRISING TRICYCLO-4H-1,4-BENZOTHIAZINE DERIVATIVES AND METHOD OF USE THEREFOR

This is a continuation of application Ser. No. 517,081, filed July 22, 1983, now abandoned.

The present invention relates to fused 4H-1,4-benzothiazines, several processes for their preparation, their use as medicaments, especially their use as inhibitors of lipoxygenase, medicaments containing them and their preparation.

It is known that the metabolites of arachidonic acid-leucotriene and slow reacting substance of anaphylaxis (SRS-A)-formed by the enzyme lipoxygenase are involved in the development of inflammatory and allergic processes, compare, for example, E. J. Goetzl, Immunology 40 709 (1980) and Medical Clinics of North America 65, 809 (1981).

Known inhibitors of lipoxygenase, such as nordihydroguaiaretic acid, 3-amino-1-(3-trifluoromethylphenyl)pyrazoline, phenidone and 5,8,11,14-eicosatetrainoic acid either act simultaneously as inhibitors of cyclooxygenase or only act at very high concentrations. Inhibition of the enzyme cyclooxygenase in arachidonic acid metabolism leads to global inhibition of prostaglandin synthesis and stimulation of the lipoxygenase route, which causes gastrotoxicity or proinflammatory and asthmatic effects. Moreover, inhibitors of lipoxygenase which are already known, such as 3-amino-1-(m-trifluoromethylphenyl)-2-pyrazoline have toxic side-effects on systemic administration (for example orally). Thus, there is a need for compounds which act orally and do not have these undesired side-effects.

Surprisingly, the fused 4H-1,4-benzothiazines according to the invention inhibit lipoxygenase at a concentration low enough for there to be little effect on cyclooxygenase.

Surprisingly, the compounds according to the invention also stimulates the synthesis of prostacyclin in arterial vessels in vitro, possibly as a consequence of their lipoxygenase-inhibitory property. The compounds have greater activity in respect of this effect than does the inhibitor of lipoxygenase mentioned, 3-amino-3-(m-trifluoromethylphenyl)-2-pyrazoline (Proc. of British Pharmacological Society 920 P (1981). The compounds according to the invention also stimulate prostacyclin synthesis in strips of rabbit aorta.

The compounds according to the invention also have an antiinflammatory effect in the model of carragenan-induced oedema when they are administered systemically, in particular orally, and locally, in particular cutaneously. They also have antimetastatic activity.

Thus, the lipoxygenase-inhibiting fused 4H-1,4-benzothiazines according to the invention can be used as medicaments for the treatment of inflammatory, allergic and cardiovascular processes. They can find use, in particular, as antiinflammatory, antirheumatic, antiatherosclerotic, antithrombotic, antiarthrotic, antiasthmatic, antiallergic, antimetastatic and gastroprotective agents. Other fields of application are the treatemtn and prevention of cerebral ischemic, transitory ischemic attacs, myocardial infarctions, strokes and arrhythmii. The compounds are also valuable in the treatment of peripheral vascular diseases and circulatory disorders in mammals.

Thus the present invention relates to compounds of the formula I defined below; and to the processes for the preparation of the compounds according to formula I detailed below; and to compounds of the general formula I for use for combating diseases, in particular as inhibitors of lipoxygenase, antiinflammatory and/or antimetastatic agents; and to medicaments containing at least one compound of the general formula I; and to the use of compounds of the general formula I for combating diseases, in particular as inhibitors of lipoxygenase, antiinflammatory and/or antimetastatic agents; and to processes for the preparation of medicaments containing at least one compound of the formula I by converting compounds of the general formula I into a suitable form for administration, optionally using conventional auxiliaries and vehicles.

The present invention relates to fused 4H-1,4-benzothiazines of the general formula I

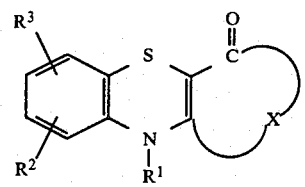

wherein
$R^1$ represents hydrogen and optionally substituted alkyl,
$R^2$ and $R^3$ represent hydrogen, optionally substituted alkyl, halogen, nitro, cyano, alkylsulphonyl, arylsulphonyl, hydroxyl, alkoxy or acyloxy and
$R^2$ and $R^3$ can be identical or different, but $R^2$ or $R^3$ do not denote bromine or $R^2$ and $R^3$ do not both denote hydrogen,
X represents alkylene (having 2 to 4 C atoms) which can be substituted once or several times by alkyl, alkoxy, aryl, fluorine or alkoxycarbonyl, or a methylene group in the alkylene bridge can also be replaced by O, S, SO, $SO_2$, NH or N-alkyl.

The present invention further relates to fused 4H-1,4-benzothiazines of the general formula I

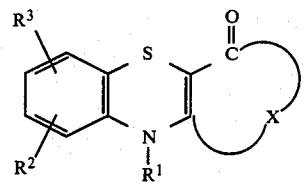

wherein
$R^1$ represents hydrogen and optionally substituted alkyl,
$R^2$ and $R^3$ represent hydrogen, optionally substituted alkyl, halogen, nitro, cyano, alkylsulphonyl, arylsulphonyl, hydroxyl, alkoxy or acyloxy and
X represents alkylene (having 2 to 4 C atoms) which can be substituted once or several times by alkyl, alkoxy, aryl, fluorine or alkoxycarbonyl, and a methylene group of the alkylene bridge can also be replaced by O, S, $SO_2$, SO, NH or N-alkyl,
for use for combating diseases, in particular as inhibitors of lipoxygenase, antiinflammatory and/or antimetastatic agents; also being contained in medicaments; and the use of these 4H-1,4-benzothiazines for combating diseases.

In the general formula I, optionally substituted alkyl, $R^1$, $R^2$ or $R^3$ represent straight-chain or branched alkyl preferably having 1 to 8, in particular 1 to 4 carbon atoms. Optionally substituted methyl, ethyl, n- and i-propyl, n-, i- and t-butyl may be mentioned as examples.

The alkyl radicals $R^1$ to $R^3$ can be substituted once to 3 times, preferably once, by the following substituents: halogen, dialkylamino, pyrrolidino, piperidino, optionally substituted aryl, alkoxy, alkylthio, alkylsulphinyl, alkylsulphonyl, —CO—$R^4$, $R^4$ representing alkyl, optionally substituted aryl; hydroxyl, alkoxy, amino, alkylamino, dialkylamino, pyrrolidino, piperidino or morpholino.

Aryl preferably having 6 to 20 carbon atoms in the aryl part is appropriate as the optionally substituted aryl $R^4$ and substituent of the alkyl radicals $R^1$ to $R^3$. Phenyl or naphthyl may be mentioned as examples. The aryl radicals can be substituted once to 3 times, preferably once, in the o-, m- or p-position by the following substituents: halogen, alkyl, alkoxy, trifluoromethyl or nitro.

Straight-chain or branched alkoxy preferably having 1 to 8, in particular 1 to 4, carbon atoms is appropriate as the optionally substituted alkoxy $R^2$ or $R^3$ and as the substituent of X. The alkoxy radicals can be substituted once to 3 times, preferably once, by the following substituents: halogen, in particular fluorine and chlorine, aryl (optionally substituted), hydroxyl, alkoxy, alkylthio or cyano.

The materials of the general formula I according to the invention can be prepared by reacting 2-aminothiophenols of the formula II with compounds of the formula III in dimethyl sulphoxide (compare J. Chem. Soc. Perkin Trans. I, 1976, 1146–49).

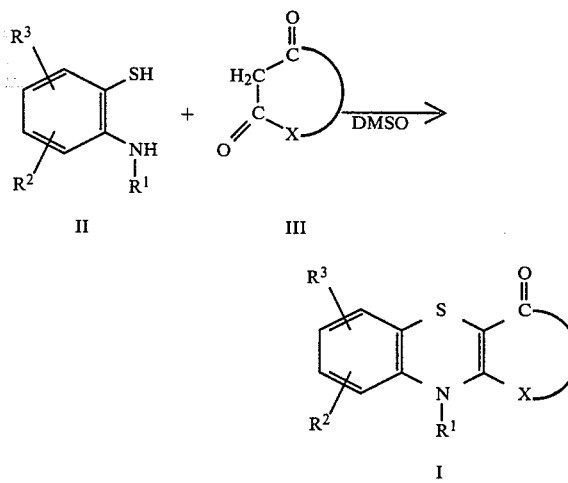

The compounds of the formulae II and III are either known from the literature or can be prepared in analogy to compounds known from the Literature. The reaction temperature can be between 50° C. and 200° C., preferably between 100° C. and 150° C. It is advantageous in some cases to work with exclusion of oxygen.

Furthermore, the materials according to the invention can be prepared by reacting disulphides of the formula IV with dicarbonyl compounds of the formula III [compare Phosphorus and Sulfur 3, 309–314, (1977)].

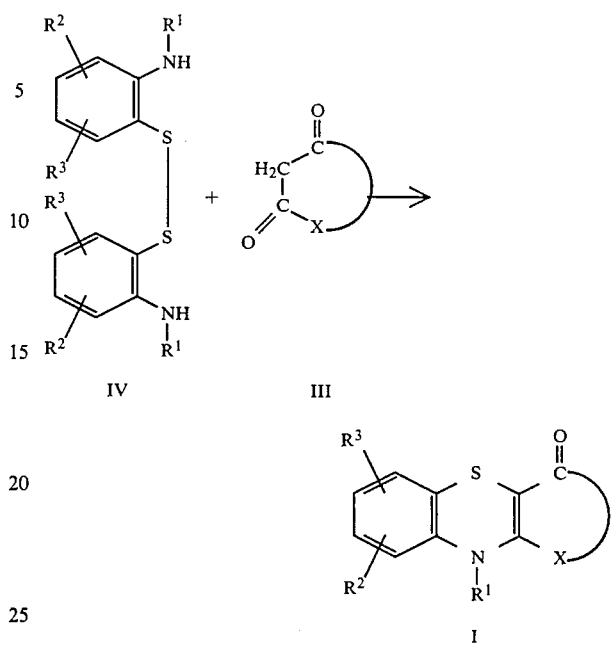

The reaction is catalysed by acids (for example p-toluenesulphonic acid).

Suitable solvents are benzene, toluene, pyridine, DMSO and DMF.

The reaction temperature can be between 20° C. and 180° C., preferably between 35° C. and 150° C.

It is advantageous to work with exclusion of oxygen.

The reaction is mostly carried out with equimolar amounts of the starting materials, but an excess (up to 110%) of dicarbonyl compound is occasionally used.

Materials of the formula I according to the invention in which $R^1$ represents alkyl (optionally substituted) can be prepared from the corresponding compounds in which $R^1$ represents H by the conventional methods of alkylation, for example by reaction with $CH_3I$, $C_2H_5$—Br or ω-bromoacetophenone.

The demonstration of the lipoxygenase-inhibitory properties of the compounds according to the invention is carried out in analogy to the method of Bailey et al., Journal of Biol. Chemistry 255, 5996, (1980) and that of Blackwell and Flower, Prostaglandins 16, 417 (1978). The metabolism of radioactively labelled arachidonic acid on washed human platelets is employed in this test method. In this in vitro test, the radioactively labelled metabolites are extracted from the reaction mixture and separated by thin-layer chromatography. The autoradiogram is evaluated on a thin-layer scanner. Under these test conditions, the labelled metabolites are separated from the unreacted archidonic acid and can then be quantitatively evaluated. The distribution of radioactivity over the cyclooxygenase products, thromboxane $B_2$ ($TXB_2$) and 12-hydroxy-5,8,10-heptadecatrienoic acid (HHT) and the lipoxygenase product 12-hydroxy-5,8,11,14-eicosatetraenoic acid (HETE) formed during metabolism under the effect of the inhibitors represents a measure of the inhibition of the enzymes.

The inhibition of lipoxygenase by the compounds according to the invention can be measured by the inhibition of HETE synthesis. It emerges that the synthesis of $TXB_2$ and of HHT is unaffected while the conversion of arachidonic acid decreases. As can be seen from the following table, the compounds according to the invention bring about a significant inhibition of platelet lipoxygenase (HETE synthesis). (Compare Table 1).

The lipoxygenase-inhibitory properties on leucocytes of the compounds according to the invention can also be demonstrated in analogy to the above text.

The polymorphonuclear leucocytes of humans and of rabbits metabolise arachidonic acid to give 5-hydroxy-5,8,11,14-eicosatetraenoic acid (5-HETE) and leucotriene B$_4$ (5S,12R-dihydroxy-6cis,8,10-trans-14cis-eicosatetraenoic acid). The inhibition of liberation of 5-HETE and leucotriene B$_4$ from the leucocytes is a measure of the lipoxygenase-inhibitory effect of the compounds according to the invention (compare Table 1).

The test with human leucocytes is carried out by the method of Borgeat and Samuelsson (j. Biol. Chem. 254, 2643, 1979 and Proc. Natl. Acad. Sci. USA, 76, 2148 (1979) and that with rabbit leucocytes by the method of Walker and Parish (Inter. Archs. Allergy appl. Immun. 66, 83, 1981).

The demonstration of the prostacyclin-stimulating effect was carried out by determining the liberation of prostacyclin after incubation of strips of rabbit aorta for one hour with the compounds according to the invention (in analogy to the method of Moncada et al., Lancet 1977, I, 18) and subsequent radioimmunological determination of the stable prostacyclin metabolite 6-keto-PGF 1 (B. M. Peskar et al. FEBS Letters 121, 25, 1980).

The compounds according to the invention are also active in vivo. This activity is demonstrated by measuring the inhibition of leucocyte migration by methods known per se (compare Higgs et al., Biochemical Pharmacology 28, 1959, (1979) and Eur. J. Pharmacol. 66, 81 (1981)).

The new active compounds can be converted in a known manner into the customary formulations, such as tablets, capsules, coated tablets, pills, granules, aerosols, syrups, emulsions, suspensions and solutions, using inert, non-toxic pharmaceutically suitable vehicles or solvents. The therapeutically active compounds should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol), glycols (for example propylene glycol and polyethylene glycol), N-alkylpyrrolidones, solid vehicles, such as, for example, natural rock powders (for example kaolins, aluminas, talc and chalk), synthetic rock powders (for example highly disperse silica and silicates), sugars (for example crude sugar, lactose and glucose), emulsifiers, such as non-ionic anionic emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular cutaneously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the line. Furthermore, lubricants such as magnesium stearate, sodium lauryl sulphate and talc can be co-used when making tablets. In the case of aqueous suspensions and/or elixirs which are intended for oral use, the active compounds can be mixed with various flavour-improving agents, coloured materials and colorants in addition to the abovementioned auxiliaries.

In the case of parenteral administration, solutions of the active compounds employing suitable liquid vehicles can be used.

In general, it has proved advantageous, in the case of intravenous administration, to administer amounts of about 0.01 to 10 mg/kg, preferably about 0.05 to 5 mg/kg of body weight daily to achieve effective results, and in the case of oral administration, the dosage is about 0.05 to 100 mg/kg, preferably 0.1 to 10 mg/kg, of body weight daily.

Nevertheless, it can at times be necessary to deviate from the amounts mentioned, and in particular to do so as a function of the body weight or of the nature of the method of administration, but also because of the species of animal and its individual behaviour towards the medicament, and the nature of the formulation of the medicament and the time or interval over which the administration takes place. Thus it can suffice in some cases to manage with less than the abovementioned minimum amount, whilst in other cases the upper limit mentioned must be exceeded. Where relatively large amounts are administrated, it can be advisable to divide these into several individual administrations over the course of the day. The above statements similarly apply for administration in both human and in veterinary medicine.

The following examples are intended to illustrate the invention in more detail: (see also Table 1).

EXAMPLE 1

7-Ethoxy-1-oxo-1,2,3,4-tetrahydrophenothiazine

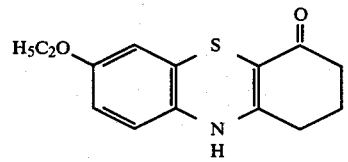

A solution of 5.4 g (0.016 mol) of 4,4'-diethoxy-2,2'-dithiodianiline and 3.6 g (0.032 mol) of 1,3-cyclohexanedione in 20 ml of dimethyl sulphoxide was heated at 110°–120° C. for one hour. After cooling, the mixture was added to 100 ml of water, and acetone was added. A precipitate formed which was filtered off with suction and recrystallised from DMF/isopropanol.

Melting point 201°–202° C.

Yield 5 g (59% of theory).

The following products can be prepared in the same manner:

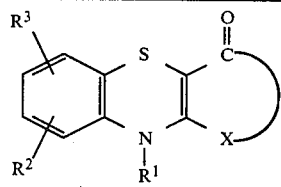

| Example | X | R¹ | R² | R³ | Melting point |
|---|---|---|---|---|---|
| 2 | $-CH_2-CH_2-CH_2-$ | H | H | H | 253° C. |
| 3 | $-CH_2-CH_2-CH_2-$ | $CH_3$ | H | H | |
| 4 | $-CH_2-CH_2-CH_2-$ | H | 7-$CH_3$ | H | 231° C. |
| 5 | $-CH_2-CH_2-CH_2-$ | H | 7-Cl | H | 250° C. |
| 6 | $-CH_2-C(CH_3)(CH_3)-CH_2-$ | H | H | H | 270° C. |
| 7 | $-CH_2-C(CH_3)(CH_3)-CH_2-$ | $CH_3$ | H | H | 153° C. |
| 8 | $-CH_2-CH_2-$ | H | H | H | |
| 9 | $-(CH_2)_4-$ | H | H | H | |
| 10 | $-CH_2-SO_2-CH_2-$ | H | H | H | |
| 11 | $-CH_2-CH_2-CH_2-$ | H | 5-$CH_3$ | 7-$CH_3$ | |
| 12 | $-CH_2-CH_2-CH_2-$ | H | 7-CN | H | |
| 13 | $-CH_2-C(CH_3)(C(O)OC_2H_5)-CH_2-$ | H | H | H | |
| 14 | $-CH_2-C(CH_3)(C(O)OC_2H_5)-CH_2-$ | H | H | H | |
| 15 | $-CH_2-O-CH_2-$ | H | H | H | |
| 16 | $-CH_2-CH_2-CH_2-$ | H | 7-$NO_2$ | H | |
| 17 | $-CH_2-CH_2-CH_2-$ | $CH_2-C(O)-Ph$ | H | H | |
| 18 | $-CH_2-CH_2-CH_2-$ | H | 7-$CH_3SO_2$ | H | |
| 19 | $-CH_2-CH_2-CH_2-$ | $C_2H_5$ | 7-$CH_3$ | H | |
| 20 | $-CH_2-CH_2-CH_2-$ | H | 7-$OCH_3$ | H | 213° C. |

TABLE 1

| Substance Example | Minimum concentration for inhibition of lipoxygenase in rabbit PMN leucocytes in g/ml |
|---|---|
| 1 | $5 \times 10^{-7}$ to $10^{-6}$ |
| 2 | $5 \times 10^{-7}$ to $10^{-6}$ |
| 4 | $5 \times 10^{-7}$ to $10^{-6}$ |
| 5 | $5 \times 10^{-7}$ to $10^{-6}$ |
| 8 | $5 \times 10^{-7}$ to $10^{-6}$ |
| 20 | $5 \times 10^{-7}$ to $10^{-6}$ |

We claim:

1. A pharmaceutical composition comprising, as an active ingredient an anti-thrombotic-effective amount of a fused 4H-1,4-benzothiazine of the formula

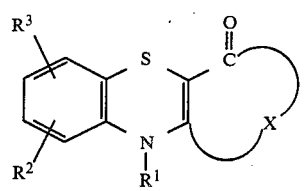

wherein
$R^1$ represents hydrogen or $C_1$-$C_8$-alkyl,
$R^2$ and $R^3$ represent hydrogen, $C_1$-$C_8$-alkyl, halogen, nitro, cyano, $C_1$-$C_8$-alkylsulphonyl, phenylsulfonyl, hydroxyl, $C_1$-$C_8$-alkoxy or carboxylic acid acyloxy and $R^2$ and $R^3$ can be identical or different, with the proviso that $R^2$ and $R^3$ do not denote bromine, or $R^2$ and $R^3$ do not both denote hydrogen, and
X represents alkylene (having 2 to 4 C atoms) which is unsubstituted or substituted by $C_1$-$C_8$-alkyl, $C_1$-$C_8$-alkoxy, phenyl, fluorine or $C_1$-$C_8$-alkoxycarbonyl, and wherein a methylene group of the alkylene bridge is replaced by O, S, $SO_2$, SO, NH or N-alkyl and an inert pharmaceutical carrier.

2. A method for treating thromboses in warm-blooded animals which comprises administering to the said animals an anti-thrombotic effective amount of an active ingredient according to claim 1 either alone or in admixture with a diluent or in the form of a medicament.

* * * * *